United States Patent [19]

Hourahane et al.

[11] Patent Number: 4,535,768

[45] Date of Patent: Aug. 20, 1985

[54] SET OF SURGICAL INSTRUMENTS

[75] Inventors: Donald H. Hourahane, Roodepoort; Angus E. Strover, Halfway House, both of South Africa

[73] Assignee: South African Inventions Development Corporation, Pretoria, South Africa

[21] Appl. No.: 411,711

[22] Filed: Aug. 25, 1982

[30] Foreign Application Priority Data

Aug. 26, 1981 [ZA] South Africa ............... 81/5918

[51] Int. Cl.³ .................. A61F 17/32; A61F 5/04
[52] U.S. Cl. ............... 128/305.1; 128/92 D; 128/92 EB; 128/92 B
[58] Field of Search ............. 128/92 A, 92 B, 92 E, 128/92 EA, 92 EB, 92 EC; 128/305.1, 305, 340, 334 R

[56] References Cited

U.S. PATENT DOCUMENTS

| 2,897,820 | 8/1959 | Tauber | 128/340 |
| 4,237,411 | 3/1981 | Cho | 128/92 EB |
| 4,244,370 | 1/1981 | Furlow et al. | 128/334 R |

FOREIGN PATENT DOCUMENTS

| 2240336 | 2/1974 | Fed. Rep. of Germany . | |
| 2078528 | 1/1982 | United Kingdom . | |
| 145977 | 7/1961 | U.S.S.R. | 128/305 |

Primary Examiner—Richard J. Apley
Assistant Examiner—David J. Isabella
Attorney, Agent, or Firm—Ladas & Parry

[57] ABSTRACT

A set of surgical instruments is provided, for threading a tow or skein of carbon fibres through a passage in bone. The set includes an elongated adaptor having a passage along its length for insertion into a passage in bone, a fish wire having a leading end provided with a hooked connector, and an extraction member with a hole therethrough the extraction member being insertable along the adaptor and through the hole in the extraction member in non-return fashion.

15 Claims, 10 Drawing Figures

SET OF SURGICAL INSTRUMENTS

This invention relates to a set of surgical instruments. In particular the invention relates to a set of surgical instruments suitable for, but not restricted to, the repair or replacement of damaged knee ligaments; and to novel components of said set of instruments.

According to the invention, broadly, a set of surgical instruments suitable for threading a surgical implant in the form of a tow or skein of carbon fibres through a hole or passage formed in a bone comprises:

an elongated adaptor having a passage or groove extending along its length for insertion into the hole or passage in the bone;

a fish-wire having a leading end provided with a forwardly tapering and rearwardly hooked connector; and an extraction member having a hole or passage therethrough, the fish-wire being insertable, leading end first, along the interior of the groove or passage of the adaptor when the adaptor is inserted in the hole or passage in the bone and its hooked connection being insertable in non-return fashion through the hole or passage in the extraction member.

Although the set of instruments is described herein with reference to implants in the form of carbon fibre tows threaded through passages in bone, it will be appreciated that the invention is not restricted thereto. Thus the instruments can be used to thread wires, sutures, cords, tows of composite materials or the like through holes or passages in soft tissue or cartilage, e.g. the soft tissue around or near a bone, and the specification is to be construed accordingly.

A set of instruments in accordance with the invention is used to thread a surgical implant in the form of a flexible cord through a hole or passage in bone or tissue, typically a cord in the form of a tow or skein of carbon fibres through a hole or passage formed in bone, by:

inserting an adaptor which is elongated and has a passage or groove extending along its length into the hole or passage formed in the bone or tissue, so that the adaptor extends therethrough;

inserting a fish-wire having a leading end provided with a forwardly tapering and rearwardly hooked connector, leading end first, along the interior of the groove or passage of the adaptor so that it extends therethrough;

inserting the hooked connector of the fish-wire in non-return fashion through a hole or passage in an extraction member after said hooked connector has emerged from the adaptor;

pulling the fish-wire further through the hole or passage in the bore or tissue by means of the extraction member; and pulling the cord through the hole or passage in the bone or tissue by means of the fish-wire.

As will emerge hereunder, the adaptor will usually be removed from the bone before the fish-wire is pulled through the bone by the extraction member, although, if an extraction member is used which is separate from and unconnected to the adaptor, the fish-wire can be pulled through the bone by the extraction member with the adaptor in position in the bone. Furthermore, it will be appreciated that the adaptor will be removed from the bone before the carbon fibre is pulled through the bone, and that the carbon fibre may be pulled in either direction through the bone, whichever is convenient.

The adaptor may be of hollow cylindrical shape and has an elongated interior guide formation, such as a passage along its interior. The adaptor usually has a tapered leading end for insertion into the bone, with the passage opening out, conveniently centrally, at the leading end through the tapered part of the leading end, conveniently at its apex. The adaptor (or the bore of the hole or passage in the bone) will be seleted so that the adaptor is a sliding fit in the hole or passage in the bone, so as to permit easy insertion therein, while being accurately aligned concentrically therewith. Although it may be curved, the adaptor will typically be straight (to conform with the shape of a straight passage in bone), being of metal such as surgical steel.

The fish-wire in turn may also be of metal, e.g. a stainless steel wire, although non-metals such as suitable plastics materials may be used instead. The fish-wire may have a leading portion which is relatively stiff, rigid and inflexible, for ease of insertion into and through the adaptor and extraction member, and a trailing portion which is relatively flexible, for easy pulling through the passage.

The hooked connector of the fish-wire may be in the form of a loop formed by the leading end of the fish-wire which is looped over once to form an eye at said leading end, and crosses over itself to close the eye, the extremity or tip of the wire pointing towards the trailing end of the fish-wire and diverging at an acute angle rearwardly to define the hook and to provide a hooked connector which tapers forwardly to the eye, the widest point of the hooked connector being wider than the hole or passage in the extraction member, whereby the hooked connector is laterally compressible upon insertion through the hole or passage of the extraction member, the material of the leading end being resiliently flexible to permit the hooked connector to spring back to its original shape upon emergence thereof from said hole or passage in the extraction member.

Withdrawal of the hooked connector from the extraction member is prevented by the rearwardly diverging tip of the fish-wire engaging the periphery of the hole or passage in the extraction member and being bent forwardly so that it and the eye extend across said hole or passage to form a kink of the nature of a T-bar which cannot enter said hole or passage. Naturally the dimensions of the hole or passage and the fish-wire itself will be selected so that the kink cannot be pulled rearwardly through the extraction member by the forces encountered in use.

The extraction member itself may merely comprise a limb having its hole or passage at or near its free end. For access to the end of the hole or passage in the bone from which the fish-wire emerges, and where the fish-wire engages the extraction member, the extraction member may be suitably shaped or curved so that it can be inserted in position through a suitably made incision in a patient (animal or human) e.g. in a patient's knee.

Provision may be made for accurate alignment of the extraction member and its hole or passage with the tapered end of the adaptor, so that the fish-wire emerging from the adaptor passes easily and accurately therethrough, preferably at a position closely spaced from said tapered end.

Thus, the set of instruments may include a frame for supporting the adaptor and the extraction member, whereby they are locatable relative to each other, so that the hole or passage in the extraction member is accurately aligned with and spaced from the adaptor, the adaptor and extraction member being movable relative to each other when on the frame. Therefore, when the adaptor is in the passage in the bone, the hole or passage in the extraction member can be accurately aligned and closely spaced from the tapered end of the adaptor. The frame may have a shape similar to that of a G-clamp, having a curved limb forming the extraction member and having the hole or passage at one end thereof, and a guide (which can conveniently act as a drilling and/or reaming guide during formation of the hole or passage in the bone) for the adaptor at the other end of the limb, the adaptor being movable along said guide towards and in alignment with the hole or passage in the extraction member.

Instead, the frame may have a similar limb, but two guides spaced along the limb, one for the extraction member which is elongated, and one for the adaptor, the extraction member and adaptor being movable along the guides to bring the opening or passage in the extraction member and the tapered end of the adaptor towards and into alignment with each other. The frame may be adapted to act as a drilling and/or reaming guide, the frame having clamping means, such as externally threaded pins, which may be provided with lock nuts and which pass through threaded passages in the frame, for clamping the frame in position, e.g. to the bone in question during drilling and/or reaming.

The set of instruments may include a drill bit and one or more cutters for providing a radius to opposite ends of a hole drilled in bone by the drill, the bit and cutter(s) being engagable with the frame for guiding thereby during use. The set may further include one or more tows of skeins of carbon fibre, each tow or skeing being engageable at one end thereof with the hooked connector of the fish wire. These tows or skeins are conveniently impregnated with gelatine or the like biologically acceptable material to hold the individual fibres together in a bundle during use, and the tows or skeins may be provided with fixing means such as studs or anchor bars for anchoring the tows in use.

The invention extends also to a fish-wire as herein described. When the wire is of stainless steel, it may be of 16-20 wire gauge. It may have a length of about 250-350 mm and its leading portion may be hardened for rigiditly, its trailing portion being annealed for flexibility, and each of these portions being about half the length of the wire.

The invention also extends to a surgical instrument comprising an adaptor, an extraction member and a frame as hereindescribed.

In use, when the adaptor and extractor member are supported on a frame as described above, on which at least one of them is movably supported, the frame will be used as a guide while moving the adaptor and extraction member relative to each other, to locate them accurately relative to each other during insertion of the hooked connector through the hole or passage in the extraction member. When the frame has clamping means. it can be clamped in position, and used as a drilling or reaming guide to preform the hole or passage in the bone or tissue, prior to threading the cord through the hole or passage.

The invention will now be described, by way of example, with reference to the accompanying diagrammatic drawings, in which.

Figure 1A:
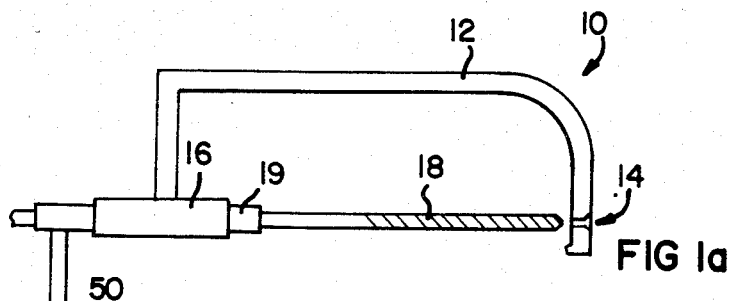
FIGS. 1A to 1E show in side elevation a set of surgical instruments according to the invention in various stages of use.

In FIG. 1 of the drawings, reference numeral 10 generally designates a set of surgical instruments according to the invention. The set of instruments 10 shown is broadly shaped like a G-clamp, having a frame 12 with an integral curved limb forming an extraction member. The extraction member of the free end of the frame 12 is provided with a passage 14 and the opposite end of the frame is provided with a tubular guide 16. The passage 14 and guide 16 are coaxially aligned.

In FIG. 1A the frame 12 is shown fitted with a drill bit 18 having a bush 19 and rotatably journalled in the guide 16.

Figure 1B:
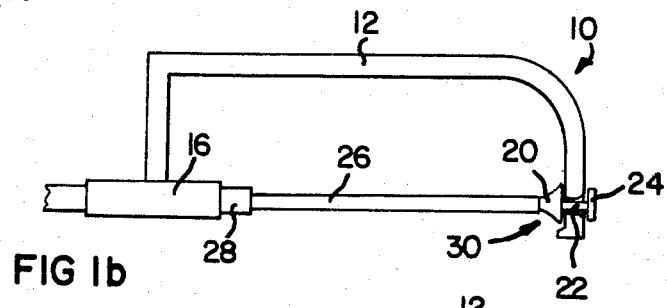

In FIG. 1B, instead of the drill bit 18, the frame 12 is shown provided with a cutter 20 rotatably mounted on a pin 22 extending through the passage 14, and having a head 24 at its end opposite the cutter 20, whereby it is located in said passage 14. The pin 22 and cutter 20 are detachable from each other, for example by the pin 22 screwing into the cutter 20. A rotatable shaft 26 having a bush 28 and journalled in the guide 16 is provided for rotating the cutter 20, the shaft 26 and cutter 20 being shown keyed together at 30 for rotation of the cutter 20 by the shaft 26, but releasable from each other in an axial direction.

Figure 1C:
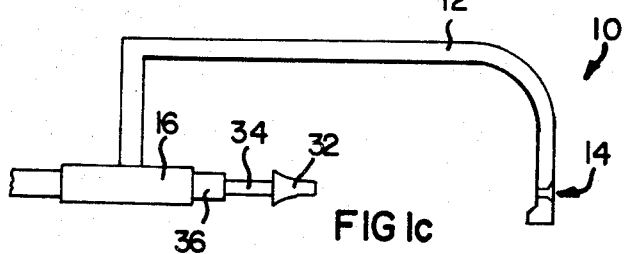

In FIG. 1C the frame 12 is shown provided with a cutter 32, fast with the end of a shaft 34 journalled in the guide 16 and having a bush 36.

Figure 1D:
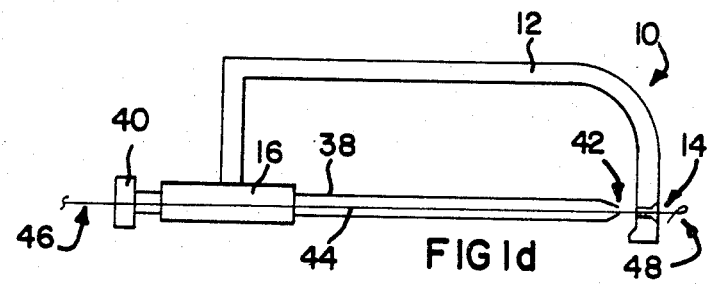

In FIG. 1D the frame 12 is shown provided with a tubular adaptor 38 extending through the guide 16 with a sliding fit, the adaptor 38 being provided with an anvil 40 axially outwardly of the guide 16, and having its opposite end tapered as at 42, its central passage opening out of the apex of said tapered end, in alignment with and adjacent the passage 14. The leading portion 44 of a fish wire 46 is shown extending through the adaptor 38, the leading end of the fish wire 46 being provided with a hooked connector 48 (described in more detail hereunder) which has passed from the adaptor 38 through the passage 14.

Figure 1E:
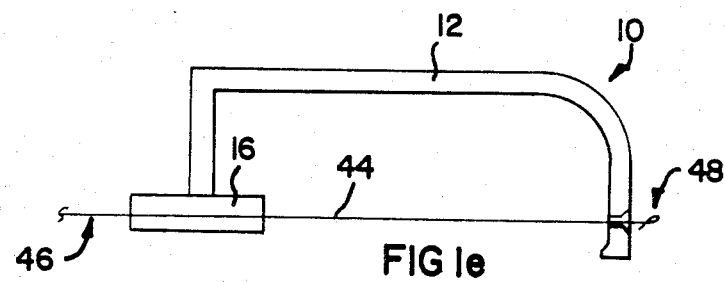

In FIG. 1E the arrangement of FIG. 1D is shown, but with the adpator 38 removed.

Figure 2:
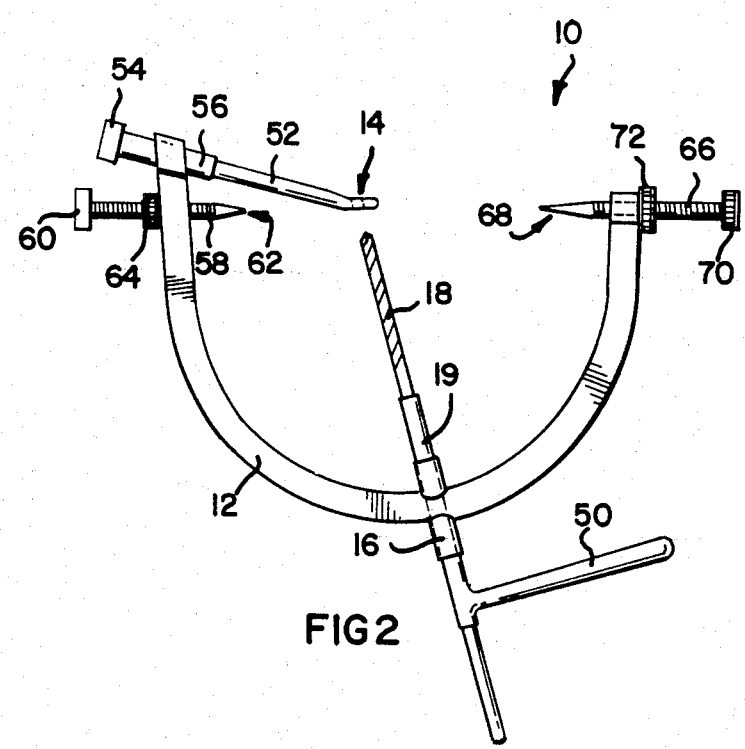
FIGS. 2 and 2A shows a side elevation of a further surgical instrument according to the invention.

In FIG. 2 the same reference numerals are used for the same parts, unless otherwise specified. The instrument of FIG. 2, while functionally similar to that of FIG. 1, is somewhat more sophisticated.

The arrangement of FIG. 2 does not resemble a G-clamp, but instead the frame 12 is broadly semi-circular in shape. The guide 16 is provided roughly midway along its length, and extending in an approximately radial direction, relative to the frame 12. A drill 18 is shown in position, and its bush 19 is shown provided with a handle 50.

A separate extraction member 52 is shown, provided with an anvil 54, and located with a sliding fit in a guide 56 at one end of the frame 12. At that end of the frame 12, and spaced slightly longitudinally inwardly from the guide 56, is provided a screw threaded pin 58 passing through a threaded passage in the frame 12. The pin 58 has, radially outwardly of the curve of the frame 12, a head 60, its radially inner end tapering to a point as at 62. Between the head 60 and the frame 12, the pin 58 is provided with a lock nut 64.

At the opposite end of the frame 12, there is a similar pin 66 having a pointed inner end at 68, a head 70 and lock nut 72. The pins 58 and 66 are coaxially and diametrically aligned with each other, relative to the frame 12.

Figure 2A:
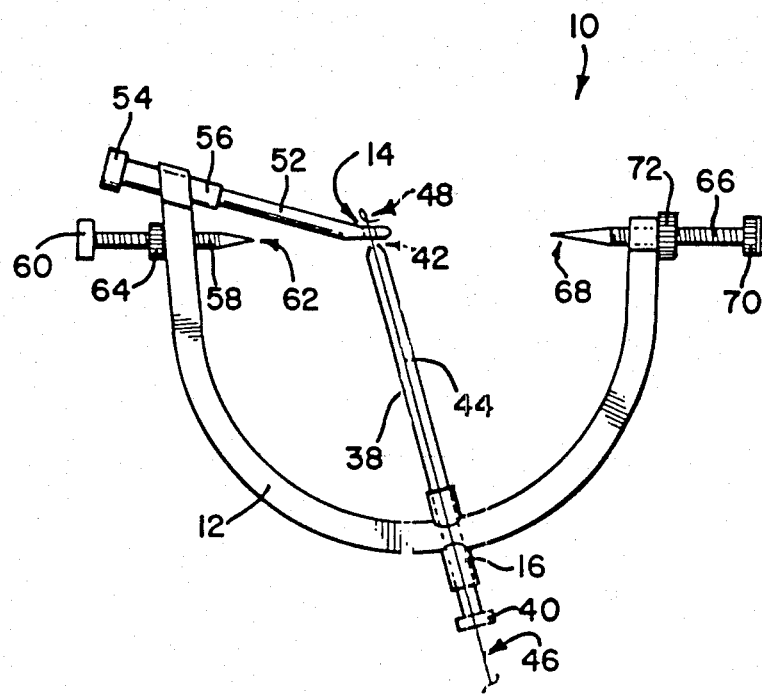

FIG. 2A shows the instrument of FIG. 2 with its drill bit and the associated bush 19 and handle 50 replaced by an adaptor 38 corresponding to that shown in FIG. 1D.

Figure 3:
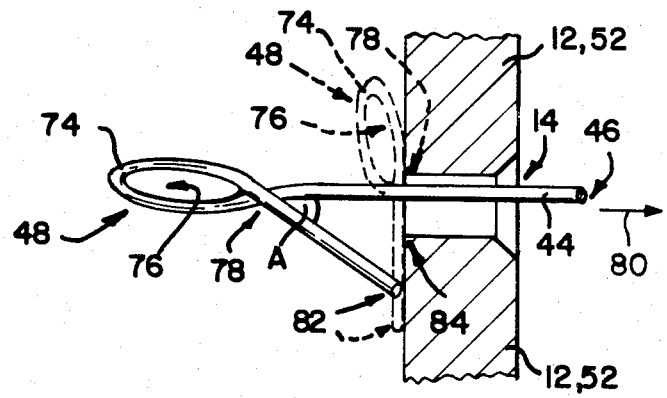
FIG. 3 shows a detail of FIGS. 1D and 1E.

In FIG. 3, a detail is shown of FIG. 1D. The hooked connector 48 is in the form of a loop 74 formed from the leading end of the fish wire 46. Said leading end is looped over once to form an eye 76 and crosses over itself at 78 to close the eye.

In FIG. 3 the fish wire 46 is shown in solid lines in its unstressed condition, and is shown in broken lines in its stressed condition, when subjected to axial tension by a pull in the direction of arrow 80.

Referring to the solid lines, the tip 82 of the fish wire, when the fish wire is unstressed, points rearwardly in the direction of arrow 80, and diverges at an acute angle A relative to the remainder of the leading portion 44 of the fish wire 46 to define a hook. A hooked connector portion 48 is thus provided at the leading end of the fish wire, which connector tapers forwardly that is, towards the eye 76, having its broadest portion, transverse to the axial direction of the fish wire 46, at said tip 82.

Figure 4:
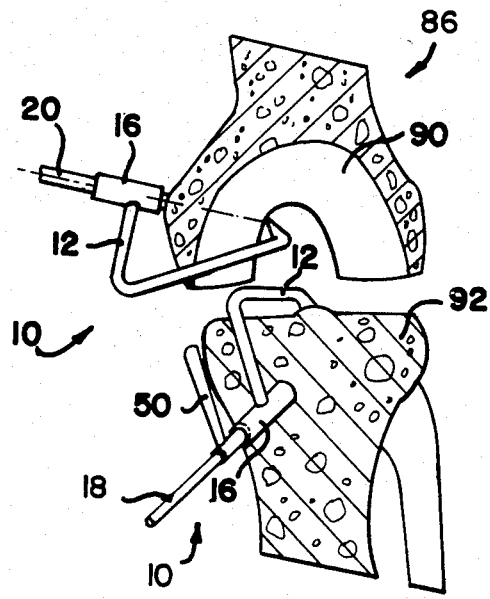
FIG. 4 shows an exploded view of a knee joint being operated upon by the set of instruments of FIG. 1.
Figure 5:
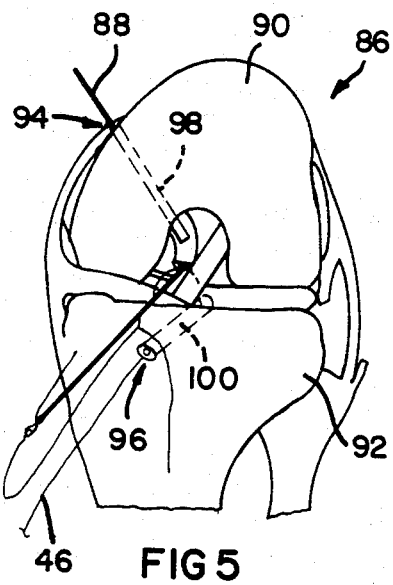
FIG. 5 shows a side elevation of the knee joint of FIG. 4 after the operation.

In use, for exsmple to thread a carbon fibre tow through a passage formed in a human knee joint (as described in more detail hereunder with reference also to FIGS. 4 and 5) the instrument 10 of FIG. 1 has the free end of its frame 12 inserted through an incision into the knee, so that the frame 12 straddles the bone in which the passage is to be formed. The drill 18 (FIG. 1A) is then used to drill the passage in the desired position, after the frame has been suitably aligned.

The instrument is then removed from the knee, and the cutter 20 is attached thereto, by detachably but securely attaching the pin 22 to the cutter 20, through the passage 14. The instrument is then inserted in the knee, and the shaft 26 inserted along the passage in the bone, until it engages the cutter 20. The distal end of the passage is then reamed by the cutter 20, by pulling the whole instrument in a direction towards the proximal end of the passage, while the shaft 26 engages and rotates the cutter 20. The mouth of the passage at the distal end of the passage is thus radiused and countersunk with a curved profile corresponding to that of the cutter 20, the shaft 26 in the passage in the bone serving accurately to align the cutter 20.

The instrument 10 is then removed and the cutter 20 is replaced by the cutter 32 (FIG. 1C), and the cutter 32 is used similarly to ream and radius the mouth at the proximal end of the passage in the bone. In this regard it will be appreciated that the cutter 32 is also detachably attached to the shaft 34, in a secure fashion.

However, with reference to FIGS. 1B and 1C, it is also contemplated that separate instruments 10 may be used for the cutters 20 and 32, to which these cutters are permanently attached, the cutter 20 to the pin 22 and the cutter 32 to the shaft 34. An interchangeable frame 12 will then only be used as shown in FIGS. 1A, 1D and 1E.

With reference to FIG. 1D, with the instrument remaining in position with the free end of the frame 12 inserted through the incision in the knee, the cutter 32 is then removed with its shaft 34, and is replaced by the adaptor 38. The adaptor 38 is inserted until the anvil 40 abuts the guide 16, at which stage the tapered end 42 is adjacent the passage 14 in the frame 12.

The fish wire 46 is then inserted through the passage (which extends through the anvil 40) in the adaptor 38 until the hooked connector 48 emerges from the tapered end 42, and passes through the passage 14 (described in more detail hereunder with reference to FIG. 3).

The adaptor 38 is then removed, by sliding it axially outwardly, and it then can be slid off the end of the fish wire remote from the hooked connector 48, and the fish wire can be cut to facilitate this. The instrument 10 is then removed, the hooked connector 48 engaging the end of the frame 12 at the periphery of the passage 14, and being drawn with the instrument 10 out of the knee joint.

As described hereunder with reference to FIGS. 4 and 5, a carbon fibre tow can be attached to either end of the fish wire 46, and the fish wire can then be used to pull the carbon fibre tow through the passage formed in the bone.

Use of the instrument 10 of FIG. 2 is similar to that of FIG. 1, the pins 58, 66 with their lock nuts 64, 72 being used firmly and accurately to locate the frame 12 relative to the bone, by screwing said pins 58, 66 inwardly by means of their heads 60, 70 until they engage opposite sides of the bone, prior to drilling the passage through the bone. However, as the extraction member 52 is separate, it need not be inserted through the incision in the knee except when the cutter 20 (see FIG. 1B) is used, or when the fish wire 46 (see FIGS. 1D and 1E) is to have its hooked connector 48 inserted through the passage 14 in the extraction member 52. In this regard, when the anvil 54 of the extraction member 52 abuts its guide 56, the passage 14 is accurately coaxially aligned with the guide 16, to permit the adaptor 38 (FIG. 1D) to have its tip 42 closely spaced from and axially aligned with the passage 14.

With reference now to FIG. 3, the broadest part of the hooked connector 48, i.e. at the tip 82, is dimensioned, and the resilience and diameter of the leading portion 44 of the fish wire 46 are such that the hooked connector 48 can be pushed through the passage 14, the fact that the leading portion 44 of the fish wire 46 is stiffened by hardening, assisting in this. During this insertion the tip 82 is pushed transversely towards the remainder of the fish wire to reduce the angle A, while the cross-over point 78 moves rearwardly in the direction of arrow 80.

Once the hooked connector passes through the passage 14, the tip 82 of the fish wire springs back to its unstressed position, annd when tension is placed on the push wire by pulling on the extraction member 12, 52, the tip 82 of the fish wire strikes said extraction member 12, 52 at the periphery of the mouth of the passage 14, as at 84. This engagement bends the tip 82 of the fish wire forwardly, in a direction opposite to arrow 80, so that it and the eye 76 extend in the fashion of a T-bar across the mouth of the passage 14, thereby effectively preventing withdrawal of the fish wire from the extraction member 12, 52. The kink so formed is too large to pass through the passage 14.

In FIGS. 4 and 5 the instrument 10 of FIG. 1 is shown in use, during the replacement of damage cruciate ligaments in a human knee joint. In this regard it will be appreciated that the instrument of FIG. 2 is in fact a posterior cruciate drill guide, adapted in accordance with the invention.

Once again, in FIG. 4, the same reference numerals are used, unless otherwise specified, and in FIGS. 4 and 5 a right knee is shown.

In FIG. 4 the device is shown in the two positions it will occupy during the drilling, reaming and radiusing of the passages, and during insertion of the fish wire.

Once the passages in the bones have been drilled in the positions shown and have had their mouths radiused, a fish wire is inserted through each passage in the bone as described above, and has one of its ends attached to a tow of carbon fibres, impregnated with gelatine. The fish wire 46 is shown in FIG. 5, and a tow of carbon fibres is shown in FIG. 5 by reference numeral 88. The tow 88 is inserted to extend from the femur 90 to the tibia 92 inside the knee joint, from a position at 94 and through the interior of the joint to emerge at 96. It can be threaded backwards and forwards more than once, if desired, and will be suitavbly anchored at or adjacent the positions 94, 96 to the outside of said bones, under the desired degree of tension.

In FIG. 5 the passages in the respective bones 90 and 92 are shown in broken lines and designated 98 and 100 respectively, and it will be appreciated that the tow 88 extends from the position 94 to the opposite end of the passage 98, through the interior of the joint 86, into the passage 100 at its end opposite the position 96, to emerge from the passage 100 at 96. One or more of the cruciate ligaments can be replaced in this fashion, the passages 98, 100 being formed so that their inner ends emerge where said ligaments are in nature attached to the bones 90, 92.

An advantage of the invention is that it provides a simple, and easily and accurately used instrument and method for threading the tows 80 in position in such surgical operations, the instrument and method being useful also in the formation of the passages in the bones. With particular reference to the embodiment of FIG. 2, it has the advantage that the ligament can be replaced through holes drilled into the knee, with only a small incision made for insertion of the extraction member 52, the interior of the knee being left otherwise undisturbed.

With reference to FIG. 3, it should be noted that the connector tapers forwardly and is forwardly deformably insertable through the passage 14, and then resiliently springs back into shape with sufficient resistance to withdrawal rearwardly, that is, in the opposite direction, to permit the fish wire to be pulled forwardly, that is, in the same direction as the taper, by the extraction member to a position where it can conveniently be gripped and used. Preferably the forwardly tapering connector has a rearwardly directed hook.

We claim:

1. A set of surgical instruments suitable for threading a surgical implant in the form of a tow of carbon fibers through a passage formed in a bone, which comprises:
   an elongated adaptor having an interior elongated guide formation extending along its length for insertion into a passage in a bone;
   a flexible fish wire having a leading end provided with a forwardly tapering and resiliently deformable connector portion; and
   a frame for supporting the adaptor, said frame including an extraction member having a passage therethrough and said frame being adapted to position said extraction member so that said passage thereof is in alignment with the interior elongated guide formation of the adaptor, the fish-wire being insertable, leading end first, along the guide formation of the adaptor when the adaptor is located in a passage in a bone and the connector portion of the fish-wire being deformably insertable in its forward direction through the passage of the extraction member, and being adapted resiliently to spring back into shape with sufficient resistance to withdrawal in the rearward direction to permit the fish-wire to be pulled in the forward direction by the extraction member.

2. A set as claimed in claim 1, in which the interior guide formation of the adaptor is a passage along the interior of the adaptor, said adaptor being of hollow cylindrical shape, the adaptor having a tapered leading end of insertion into the bone, and the passage opening out at the leading end of the adaptor through the tapered part of the leading end.

3. A set as claimed in claim 2, in which the adaptor is straight and is of surgical steel.

4. A set as claimed in claim 1, in which the fish-wire is a stainless steel wire.

5. A set as claimed in claim 1, in which the connector portion of the fish-wire is relatively stiff, rigid and inflexible, for ease of insertion into and through the adaptor and extraction member, and a trailing portion of said fish-wire is relatively flexible, for easy pulling through the passage.

6. A set as claimed in claim 1, in which the connector portion of the fish-wire is in the form of a loop formed by the leading end of the fish-wire which is looped over once to form an eye at said leading end, and crosses over itself to close the eye, the tip of the wire pointing towards the trailing end of the fish-wire and diverging at an acute angle rearwardly from the crossed-over portion of the fish-wire to define a hook and to provide a hooked connector which tapers forwardly to the eye, the widest point of the hooked connector being wider than the passage of the extraction member, whereby the hooked connector is deformably compressible upon insertion through the passage of the extraction member, the material of the leading end being resiliently flexible to permit the hooked connector to spring back to its original shape upon emergence thereof from said hole or passage in the extraction member.

7. A set as claimed in claim 1, in which the frame is adapted to act as a drilling guide, the frame having clamping means for clamping the frame in position relative to a bone being drilled during drilling.

8. A set as claimed in claimed in claim 7, which includes a drill bit and at least one cutter for providing a radius to opposite ends of a hole drilled in bone by the drill, the bit and cutter being engageable with the frame for guiding thereby during use.

9. A set as claimed in claim 1, which includes at least one tow of carbon fibres, each tow being engagable at one end thereof with the fish-wire.

10. A flexible fish-wire suitably for threading a surgical implant in the form of a tow of carbon fibres through a passage formed in bone and which fish-wire has a leading end provided with a forwardly tapering and resiliently deformable connector portion, the fish-wire having a leading portion which is relatively stiff, rigid and inflexible and a trailing portion which is relatively flexible.

11. A fish-wire as claimed in claim 10, which is of stainless steel and in which the connector portion is in the form of a loop formed by the leading end of the fish-wire which is looped over once to form an eye at said leading end, and crosses over itself to close the eye, the tip of the wire pointing towards the trailing end of the fish-wire and diverging at an acute angle rearwardly from the crossed-over portion of the fish-wire to define a hook and to provide a hooked connector which tapers forwardly to the eye, the material of the leading end being resiliently flexible to permit the hooked connector to spring back to its original shape after it has been deformably compressed.

12. A set as claimed in claim 1, in which the frame includes a guide along which the elongated, adaptor is movable, the extraction member being provided by a curved integral limb of the frame and the passage of the extraction member being aligned with the guide.

13. A set as claimed in claim 1, in which the extraction member is movable relative to the frame, and in which the frame includes two guides spaced from each other, namely one guide along which the adaptor is movable, and another guide along which the extraction member is movable, the extraction member being elongated and having an anvil spaced along the length of the extraction member from the passage through the extraction member, the anvil being abuttable against the guide for the extraction member when the passage through the extraction member is aligned with the guide for the adaptor.

14. A method of threading a surgical implant in the form of a flexible core through a passage in a bone, which comprises:

inserting an adaptor supported on a frame into the passage formed in the bone so that the adaptor extends therethrough, the adaptor being elongated and having an elongated interior guide formation extending along its length;

inserting a flexible fish-wire having a leading end provided with a forwardly tapering and resiliently deformable connector portion, leading end first, along the guide formation of the adaptor so that the fish-wire extends along the length of the adaptor and the connector portion emerges from the guide formation at the distal end of the adaptor;

inserting the connector portion of the fish-wire forwardly through a passage in an extraction member included with the frame after said connector portion has emerged from the adaptor so that the connector portion is resiliently deformed as it passes through the passage in the extraction member and springs back into shape when it emerges therefrom;

pulling the fish-wire forwardly through the passage in the bone by means of the extraction member;

attaching the fish-wire to the cord; and threading the cord through the passage in the bone by means of the fish-wire, the frame being used as a guide for the adaptor and extraction member so as to align the guide formation in the adaptor with the passage in the extraction member before insertion of the connector portion of the fish-wire through the passage of the extraction member, and the adaptor being removed from the passage in the bone before threading the cord through the passage in the bone.

15. A method as claimed in claim 14, which includes clamping the frame in position relative to the bone, and using said frame as a drilling guide to preform the passage in the bone prior to threading the cord through the passage.

* * * * *